US008636957B2

(12) United States Patent
Wellinghoff et al.

(10) Patent No.: US 8,636,957 B2
(45) Date of Patent: Jan. 28, 2014

(54) SPIRAL, MICROCHANNELED CHROMATOGRAPHIC COLUMN AND DETECTION SYSTEMS

(75) Inventors: Stephen Thomas Wellinghoff, San Antonio, TX (US); Kent Edward Coulter, Fair Oaks Ranch, TX (US)

(73) Assignee: Southwest Research Institute, San Antonio, TX (US)

( * ) Notice: Subject to any disclaimer, the term of this patent is extended or adjusted under 35 U.S.C. 154(b) by 631 days.

(21) Appl. No.: 12/437,398

(22) Filed: May 7, 2009

(65) Prior Publication Data

US 2010/0281948 A1 Nov. 11, 2010

(51) Int. Cl.
*G01N 30/60* (2006.01)

(52) U.S. Cl.
USPC ............ 422/89; 422/502; 422/503; 73/23.35; 73/23.39; 96/101; 96/104

(58) Field of Classification Search
USPC ...................... 422/70, 502, 503, 89; 436/161; 73/61.52, 61.53, 23.35, 23.39; 96/101, 96/104; 210/198.2, 656
See application file for complete search history.

(56) References Cited

U.S. PATENT DOCUMENTS

| | | | |
|---|---|---|---|
| 4,496,461 A | | 1/1985 | Leeke et al. |
| 5,059,654 A | * | 10/1991 | Hou et al. ................ 525/54.1 |
| 5,814,128 A | | 9/1998 | Jiang |
| 5,948,361 A | * | 9/1999 | D'Aragona et al. ............ 422/98 |
| 6,294,090 B1 | | 9/2001 | Nussbaumer et al. |
| 6,706,519 B1 | * | 3/2004 | Kellogg et al. ............ 435/287.2 |
| 7,118,712 B1 | * | 10/2006 | Manginell et al. ............. 422/69 |
| 7,223,364 B1 | * | 5/2007 | Johnston et al. ............ 422/68.1 |
| 2004/0026322 A1 | * | 2/2004 | Nussbaumer et al. ........ 210/644 |

OTHER PUBLICATIONS

Harper, "The use of thermal desorption in monitoring for the chemical weapons demilitarization program," J Environ Monit. Oct. 2002; 4(5):688-94.
Libardoni, "Analysis of human breath samples with a multi-bed sorption trap and comprehensive two-dimensional gas chromatography (GC x GC)," Journal of chromatography, 2006, vol. 842, No. 1, pp. 13-21.
Kortunov, "Intracrystalline Diffusivities and Surface Permeabilities Deduced from Transient Concentration Profiles: Methanol in MOF Manganese Formate," J. Am. Chem. Soc. 2007, 109 (25), 8041-8047.
Tian, "Microfabricated Preconcentrator-Focuser for a Microscale Gas Chromatograph," Journal of microelectromechanical systems, 2003, vol. 12, No. 3, pp. 264-272.

(Continued)

*Primary Examiner* — Jan Ludlow
(74) *Attorney, Agent, or Firm* — Grossman, Tucker et al

(57) ABSTRACT

The present disclosure relates to a spirally wrapped chromatographic structure, a system incorporating such structure and a method of providing such structure. The structure may include an absorber layer having a first surface and a second surface, wherein one or a plurality of channels are defined in the first surface. The structure may also include a support layer having a first surface and a second surface, the first surface of the support layer disposed on the second surface of the absorber layer, wherein the absorber layer and the support layer comprise a spiral configuration such that at least a portion of the first surface of the absorber layer contacts at least a portion of the second surface of the support layer.

17 Claims, 7 Drawing Sheets

(56) References Cited

OTHER PUBLICATIONS

Manginell, et al., "Two-Dimensional Modeling and Simulation of Mass Transport in Microfabricated Preconcentrators," IEEE Sensors Journal, vol. 7, No. 7, Jul. 2007.

Ruiz et al., "Membrane-suspended microgrid as a gas preconcentrator for chromatographic applications," Sensors and Actuators A 135 (2007) 192-196.

Mueller, et al., "Metal-organic frameworks—prospective industrial applications," J. Mater. Chem., 2006, 16, 626-636.

Stumpf, "Dynamic gas flow measurements on aerogels," Journal of Non-Crystalline Solids 145 (1992) 180-184.

Kong, et al., "Gas permeability of carbon aerogels," J. Mater. Res., vol. 8, No. 12, Dec. 1993, pp. 3100-3105.

Luo, "Adsorption and electrothermal desorption of organic vapors using activated carbon adsorbents with novel morphologies," Carbon 44 (2006) 2715-2723.

Kiwi-Minsker, et al., "Microstructured reactors for catalytic reactions," Catalysis Today 110 (2005), pp. 2-14.

Walter, et al., "Mass transfer limitations in microchannel reactors," Catalysis Today 110 (2005), pp. 15-25.

Johannessen, et al., "Optimal Distributor Networks in Porous Catalyst Pellets. I. Molecular Diffusion," Ind. Eng. Chem. Res., 2007, 46 (12), 4245-4256.

Bae, et al., "Microchennel development for autothermal reforming of hydrocarbon fuels," Journal of Power Sources 139 (2005) 91-95.

Sarkar, et al., "Deposition of polymer coatings onto SAW resonators using AC electrospray," Sensors and Actuators B 114 (2006) 756-761.

Yeo, "A New ac Electrospray Mechanism by Maxwell-Wagner Polarization and Capillary Resonance," Physical Review Letters, vol. 92, No. 13 (2004).

Kim, et al., "A PMMA optical diffuser fabricated using an electrospray method," Appl. Phys. A 86, 347-351 (2007).

Besra, et al., "A review on fundamentals and applications of electrophoretic deposition (EPD)," Progress in Materials Science 52 (2007) 1-61.

Shan, et al., "Electrophoretic deposition of nanosized zeolites in nom-aqueous medium and its application in fabricating thin zeolite membranes," Microporous and Mesoporous Materials 69 (2004) 35-42.

Hayashi, et al., "Preparation of Gas Diffusion Electrodes by Electrophoretic Deposition," Journal of the Electrochemical Society, 151 (3) A354-A357 (2004).

Gu, et al., "3D Porous Metal-organic Framework Exhibiting Selective Adsorption of Water over Organic Solvents," Inorg. Chem., 2007, 46 (15), 5835-5837.

Ni, et al., "Metal-Organic Frameworks as Adsorbents for Trapping and Preconcentration of Organic Phosphonates," Anal. Chem., 2007, 79 (4), 1290-1293.

Committee on Monitoring at Chemical Agent Disposal Facilities, National Research Council, "Monitoring at Chemical Agent Disposal Facilities," The National Academies Press, 2005 (104 pages); available at http://www.nap.edu/openbook.php?record_id=11431&page=1.

Coulter, et al., "GCxGC and Preconcentrator-Input from Steve Wellinghoff Phases 02.001 and 02.002. GC x GC, Preconcentrator Coating Report 9," Design of GCXGC and Preconcentrator Substrate, not dated, (3 pages).

Wellinghoff, "Phases 02.001 and 02.002. GC x GC, Preconcentrator Fabrication March Report 12 from Steve Wellinghoff et al.," date unknown (51 pages).

Henk, et al., "Gas Chromatographic Techniques for the Analysis of Chemical Warfare Agents," available at http://chromatographyonline.findanalytichem.com/lcgc/Column:+Coupling+Matters/Gas-Chromatographic-Techniques-for-the-Analysis-of/ArticleStandard/Article/detail/414752; retrieved on May 12, 2009 (7 pages).

Tian, et al., "Multiple-Stage Microfabricated Preconcentrator-Focuser for Micro Gas Chromatography System," Journal of Microelectromechanical Systems, vol. 14, No. 3, Jun. 2005 pp. 498-507.

* cited by examiner

SPIRAL, MICROCHANNELED CHROMATOGRAPHIC COLUMN AND DETECTION SYSTEMS

CROSS REFERENCES TO RELATED APPLICATIONS

None.

FIELD OF THE INVENTION

The present disclosure relates to gas chromatography and, in particular, to a spiral, microchanneled chromatographic column and a method of making thereof that may be utilized in a relatively mobile detection system.

BACKGROUND

Gas chromatography (GC) is an example of an analytical technique that may be used to aid in the determination of the composition of a compound. The technique allows for the separation of one or more constituents or analytes in a sample. The sample may be collected and passed through a column including a stationary phase by a carrier or mobile phase. The various constituents of the sample may travel at different rates through the column due to the chemical and physical properties of the constituents as well as the interaction of the constituents with the stationary phase. As the constituents exit the column the amount of each constituent may be determined and the composition of the constituents may be identified, depending on the type and arrangement of detectors provided. A variation on the above has been developed, wherein two or more columns are provided in a series, otherwise known as GCxGC. Each column may include a different stationary phase, which may help resolve separations wherein the constituents coelute, i.e., do not separate, in one stationary phase but may separate in another stationary phase.

GC has been found to be useful in detectors for identifying various compositions, such as chemical warfare agents. Detectors have been identified that may be reasonably accurate, detect compositions at relatively low threshold concentrations and provide a high detection probability. However, the detectors may be relatively large and bulky and require a relatively high amount of power or may be relatively small and light but lack sensitivity.

SUMMARY OF THE INVENTION

An aspect of the present disclosure relates to a spirally wrapped chromatographic structure. The structure may include an absorber layer having a first surface and a second surface, wherein one or a plurality of channels are defined in the first surface. The structure may also include a support layer having a first surface and a second surface, the first surface of the support layer disposed on the second surface of the absorber layer, wherein the absorber layer and the support layer comprise a spiral configuration such that at least a portion of the first surface of the absorber layer contacts at least a portion of the second surface of the support layer.

Another aspect of the present disclosure relates to a system for chromatographic analysis. The system may include at least one chromatography column, wherein the chromatography column comprises a spirally wrapped structure and a detector. The spirally wrapped structure may include an absorber layer having a first surface and a second surface, wherein one or a plurality of channels are defined in the first surface. The spirally wrapped structure may also include a support layer having a first surface and a second surface, the first surface of the support layer disposed on the second surface of the absorber layer, wherein the absorber layer and the support layer are rolled into a spiral configuration such that at least a portion of the first surface of the absorber layer contacts at least a portion of the second surface of the support layer.

A further aspect of the present disclosure relates to a method of forming a spirally wrapped chromatography structure. The method may include providing a substrate including one or more channels defined on a first surface, coating the substrate with a release layer and disposing an absorber layer over the release layer, having a first surface contacting the release layer and a second surface. The method may also include disposing a support layer on the second surface of the absorber layer; and removing the substrate.

Yet another aspect of the present disclosure relates to a method of providing a spirally wrapped chromatography structure. The method may include coating an embossed film material with a release layer, coating on the release layer an electrically resistant material, coating the electrically resistant material with absorber material, and wrapping the coated product, forming a spirally wrapped chromatographic structure comprising a plurality of absorber layers including one or more channels therein which overlap one another in a continuous manner wherein the channels extend continuously around an axis.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

The present disclosure relates to gas chromatography and in particular to a spirally configured, microchanneled chromatographic column, as well as other structures, a method of making such a column and a detector system in which the column may be utilized. While the system may include a single gas chromatography column, the system may include an additional column, 2D GC or GCxGC, in which each column may exhibit different physical properties (e.g. length) and may include different stationary phases.

Figure 1:
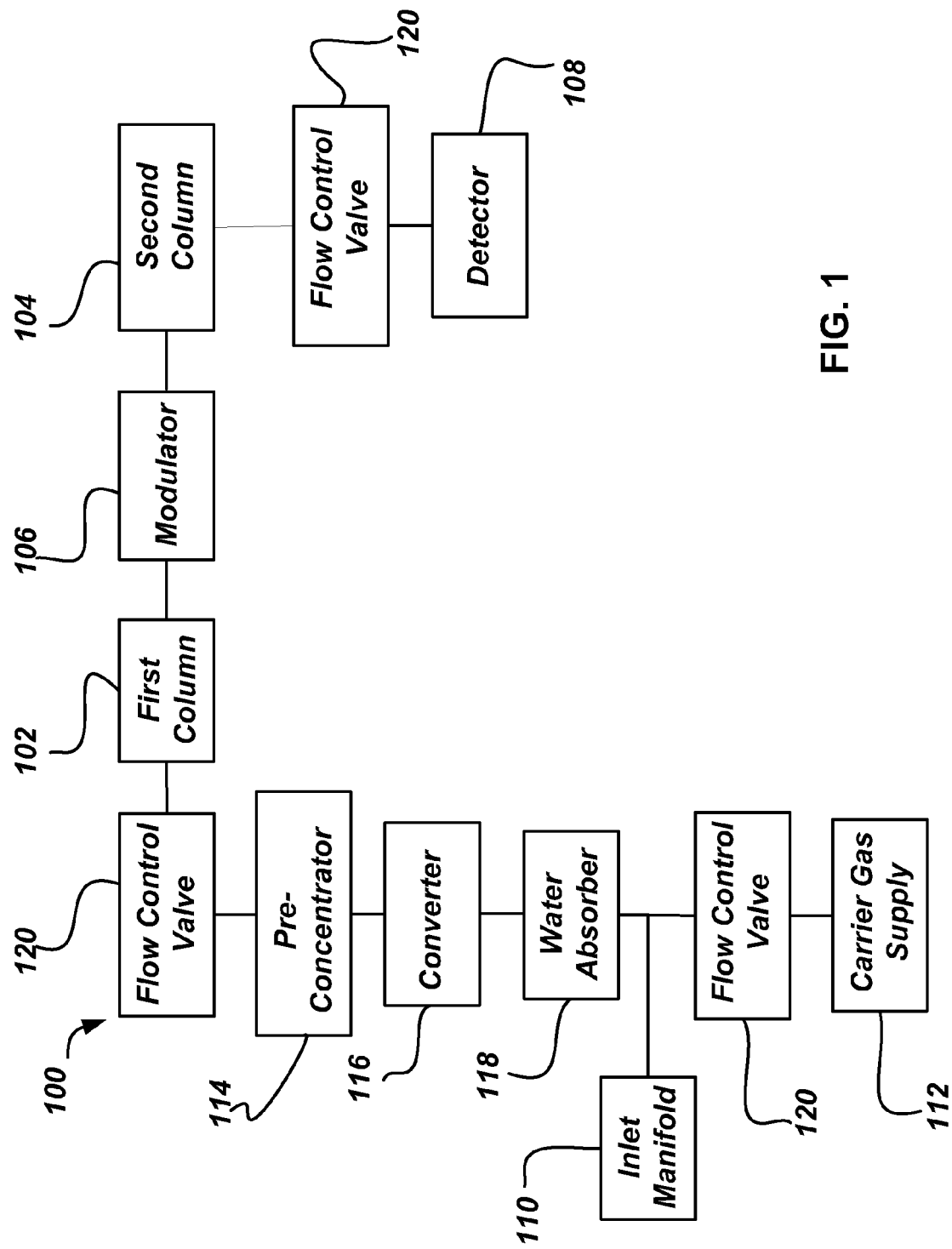
FIG. 1 illustrates an example of a 2D gas chromatography system.

2D gas chromatography (GCxGC) may be understood as a technique of separating the various constituents in a sample. FIG. 1 illustrates an example of a 2D gas chromatographic setup, examples of the individual components are discussed further below. The system 100 may generally include a first chromatographic column 102, a second chromatographic column 104, a thermal modulator or pressure modular 106 or other or splitter between the columns and a detector 108.

In addition, a system may include an inlet or manifold 110 that may provide a gas sample to the first column 102 and/or a second column 104. A carrier gas supply 112 may be provided in fluid communication with the inlet 110 and/or the first column 102, which may supply carrier gas to carry the gas sample through the system. A system may also optionally include one or more concentrators 114 for concentrating the sample before or after entering the chromatographic columns, converters 116 for chemically converting components in a sample, water scrubbers or traps 118 for removing water from a gas sample, as well as various flow control valves 120 for regulating the rate of flow or pressure of the sample in the system. For example, a one way valve may be provided between the inlet and the first chromatography column and/or between the carrier gas supply and inlet and/or first chromatography column to prevent back flow of the sample into the carrier gas supply. In addition, a pressure valve and/or one way valve may be provided at the end of the column to regulate pressure and/or prevent back flow of the eluted sample into the column.

Figure 2:
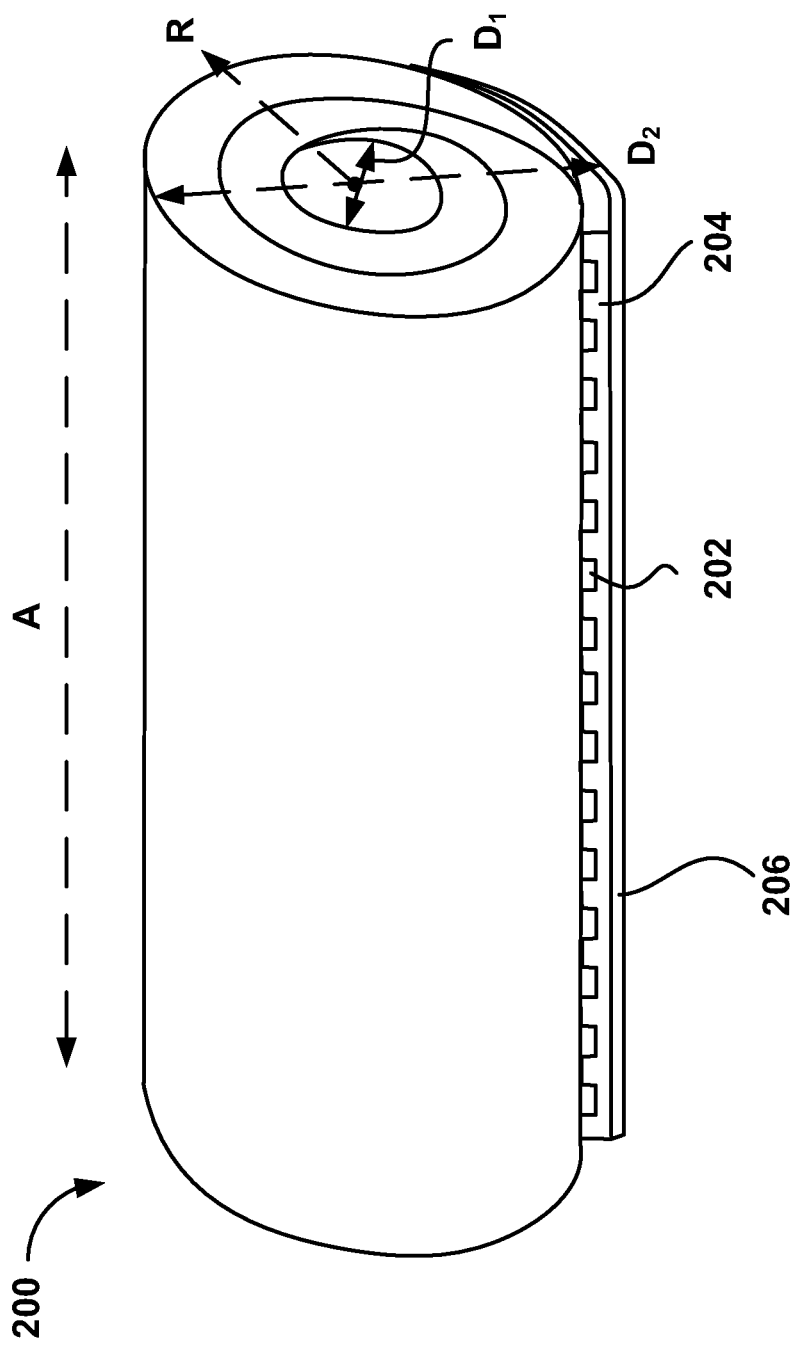
FIG. 2 illustrates an example of a spirally wrapped structure.

In one example, components of the system such as the chromatographic columns, pre-concentrator, post-concentrator, converter, and/or thermal or pressure modulator may be fabricated in the form of spirally wrapped chromatographic structures, illustrated in FIG. 2. Accordingly, a spirally-wrapped chromatographic structure may be understood herein as a plurality of absorber layers including one or more channels therein which are configured to overlap one another in a continuous manner (i.e. the channels extend continuously around an axis). Each layer may be concentric or non-concentric with respect to the axis they may surround. In general, the structures 200 may include a series of channels 202 for gas passage in an absorbent material 204 including a supportive metal or ceramic coating 206, which may then be spirally wrapped. In one example, the channels may be arranged in a relatively parallel manner and may either extend axially "A" along the length of the structure, or radially "R" around the radius of the structure.

In one example of forming the spiral wrapped structures, a substrate may be provided upon which the structure may be formed, including a number of features that may be utilized to define the features in the structure, such as channels or capillaries. The substrate may be formed from, for example, ceramic material, metal material, or polymeric material, such as polyester, polyamide, polycarbonate. Then various features may be applied to the substrate by the application of heat and/or pressure through the use of a patterning tool. The patterning tool may include features that define the capillary channels or other features that are to be formed on the film, including, for example, passageways forming the channels. Examples of patterning tools may include a calendar roll, compression press, a stamp, or other molds and tools that may form features within the substrate surface.

Figure 3:
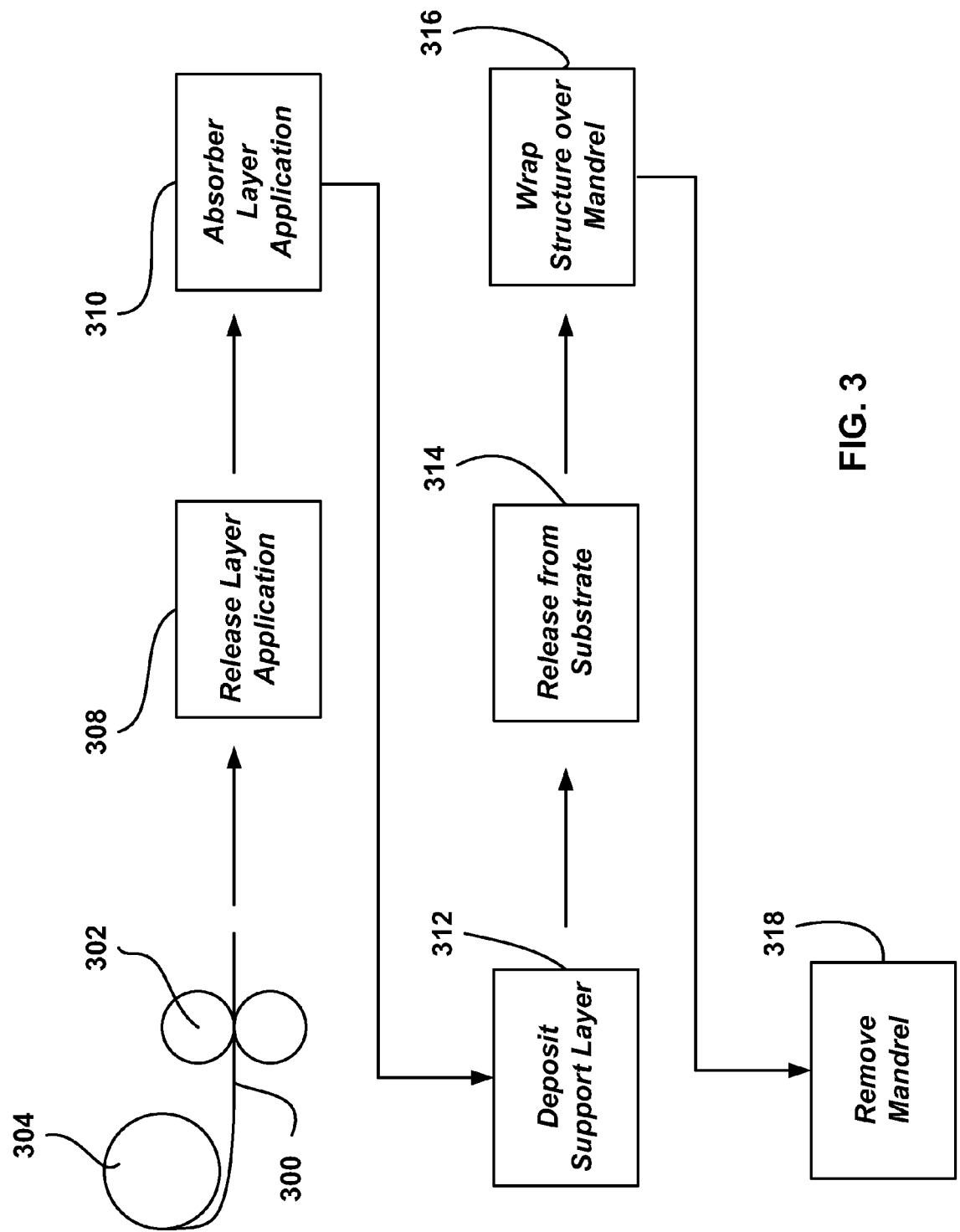
FIG. 3 illustrates an example of a method illustrated in flow chart form of forming a spirally wrapped structure.
Figure 4:
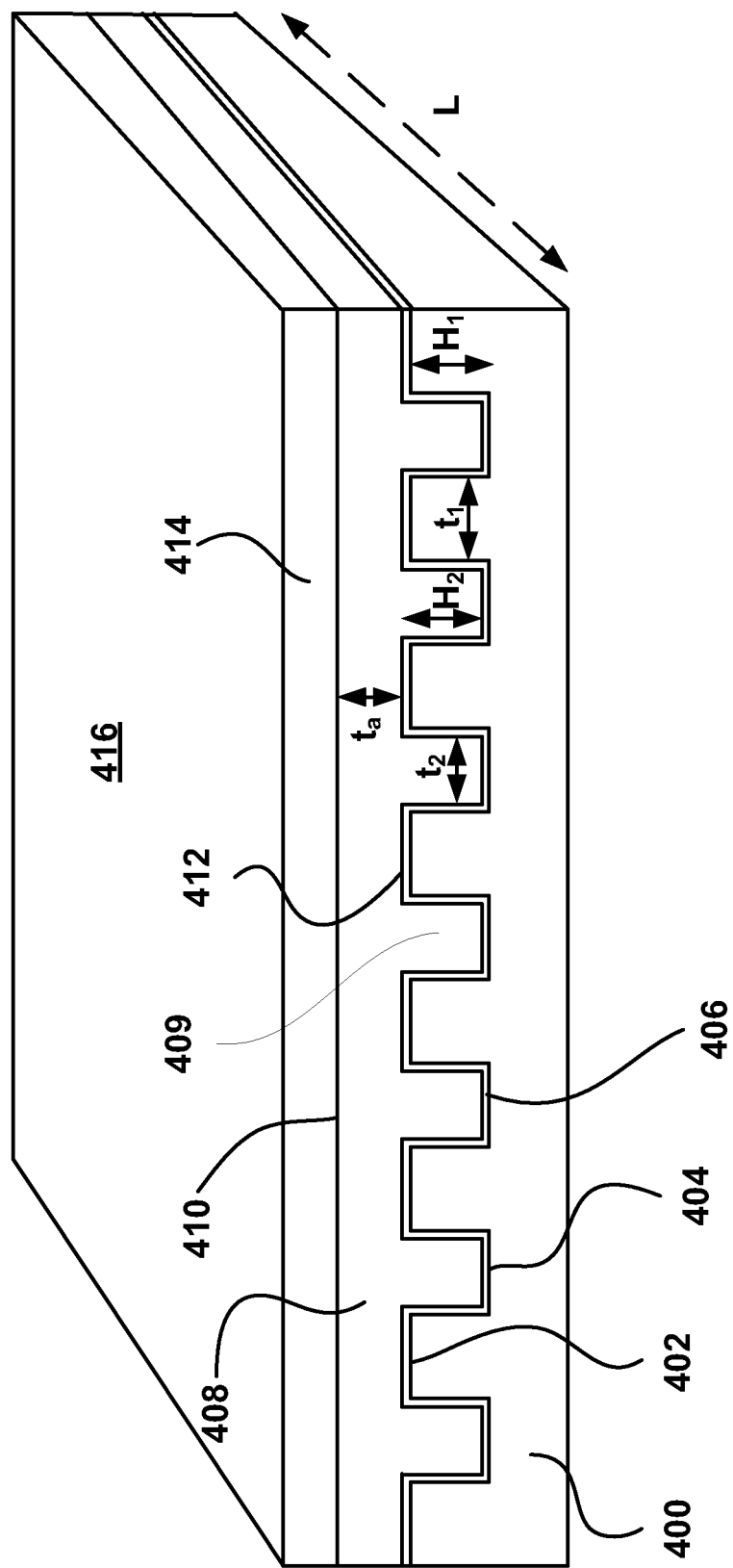
FIG. 4 illustrates an example of a support layer including a release layer, an absorber layer and a support layer.

FIG. 3 illustrates the passage of a substrate 300 through a set of calendar rolls 302, forming a pattern on or in the substrate. The substrate may be feed from a feed roll 304 or may be fed directly from, for example, an extrusion film or sheet line. FIG. 4 illustrates an embossed substrate 400 including features 402 on the surface 404 of the substrate. The features of the substrate may then serve to form the features of the absorbent material.

It may be appreciated that the features may have dimensions in the range of 0.1 Mm to 10,000 Mm (or 10 mm) in thickness ($t_1$) or height ($H_1$), including all values and increments therein, and a length (L) that may be continuous in the machine direction (MD) or cross-machine direction (CD) of the substrate or as small as 0.1 μm. The thickness or height may be understood as the largest dimension of the feature from the surface 404. It is worth noting that although the features in FIG. 4 are illustrated as being relatively square and having a raised portion 402 projecting from a surface 404 of the substrate, other geometries are contemplated. For example, the features may be triangular in form, oval, and/or round, while still, e.g., having a thickness (largest linear dimension) of 0.1 μm to 10,000 μm. The features may also be recessed into the substrate surface 404.

Furthermore, it should be noted that the recited values of thickness or height as well as length of the features in the substrate will define a corresponding feature in the absorbent material of the same dimensions. Accordingly, as illustrated, the absorbent material 408 may have a raised portion 409 that includes dimensions in the range of 0.1 μm to 10,000 μm (or 10 mm) in thickness ($t_2$) or height ($H_2$), including all values and increments therein, and a length (L) that may be continuous in the machine direction (MD) or cross-machine direction (CD) of the substrate or as small as 0.1 μm Referring again to FIG. 3, once the substrate 300 has been patterned, a release layer may be applied to the patterned surface 308. The release layer (illustrated in FIG. 4 as 406) may include an inorganic or organic salt. It may be appreciated that the release layer may be relatively thin, i.e., 0.001 μm to 100 μm in thickness, including all values and increments therein. It may also be appreciated that the release layer may be applied such the release layer does not substantially alter the desired size and shape of the features to be formed in the absorbent material. The release layer may be applied in a solution including the release composition and one or more solvents, from which the solvent may be removed leaving behind the release layer.

An absorber layer (illustrated in FIG. 4 as 408) may then be applied to the substrate at 310. The absorber layer may coat the substrate forming channels as well as any other features, for use in the resulting spirally wrapped structure. The absorber layer may be applied such that a relatively flat surface (illustrated in FIG. 4 as 410) may be developed opposite the surface in which the features are provided (illustrated in FIG. 4 as 412). It may be appreciated that reference to a relatively flat surface may be understood as reference to a surface that may not incorporate features and/or include relatively little to no asperities, i.e., features that raise up from or are depressed into the surface by 2% or less of the total layer thickness. It may also be appreciated that in some examples, featureless portions of the absorber layer may exhibit a variation in thickness ($t_a$) of less than 5%, including all values and increments in the range of 0.1 to 5%. The absorber layer may have a thickness in the range of 0.1 μm to 10,000 μm, including all values and increments therein.

As alluded to above, the absorber may amount to a stationary phase layer may be apolar, polar, or polarizable. Reference to stationary phase may be understood as the immobile phase in a chromatography separation column. It may also be understood herein that apolarity, polarity and polarizable is reference to the effects due to hydrogen bonding, dipole moment, acid-base properties, and molecular configuration, which may be expressed in terms of McReynold's values x', y', z', u' and s'. Values x', y', z', u' and s' represent 5 probes, benzene, butanol, 2-pentanone, nitropropane and pyridine, and the evaluation of their relative retention times versus their retention index (100 times the number of carbon atom in the probe molecule). Phases that provide individual McReynold's values between 0 to 100 may be considered relatively nonpolar, phases that provide individual values between 100 to 400 may be considered to be of relative intermediate polarity and values over 400 indicate relatively high polar phases.

It may be appreciated, for example, that squalene (as an absorber or stationary phase)) exhibits McReynold's numbers of x'=0, y'=0, z'=0, u'=0 and s'=0. Other absorber or stationary phases may include, e.g., poly(dimethylsiloxane), or methylsiloxane. Examples of polar compounds may include polyethyleneglycol (PEG), PEG in combination with terephthalic acid, diethylene glycol succinate, amino alcohol, or dicyanoallyl silicone. Examples of polarizable compounds or compounds exhibiting intermediate polarity may include vinyl methyl polysiloxane, methylcyano ethyl silicone, polyalkylene glycol or poly(diphenyldimethyl siloxane) 65%:35% or 75%:25% diphenyl to dimethyl. Furthermore, the absorber layer may include activated carbon, AgF containing ceramic or polymer, silica or other materials, such as metal organic frameworks. Metal organic frameworks may include those which are thermally reversible water specific, organic phosphonate sensitive, particulate containing polycarbosilanes and siloxanes substituted with hexafluoroisopropanol groups and pyridine substituted aromatics.

In other embodiments, the absorber layer may include fluoroalcohol polycarbosilanes. Such may be understood as having the formula:

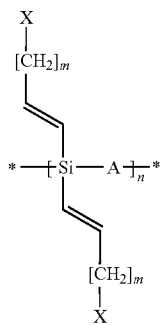

In the above, n may have a value of 10-10,000 m may have a value of 1-50, and X may be a carbon atom or an aromatic ring which carbon atom or aromatic ring includes at least one of an alcohol group (—OH) and a —CF$_3$ group. In addition, A may be selected from the following: —O—, —(CH$_2$)$_x$— where x may have a value of 1-3, and/or A may be an aromatic group. One particularly preferred polycarbosilanes include fluoroalcohol carbosilanes available from SeaCoast Science of Carlsbad, Calif. under the product designation SC-F102 which has the following formula:

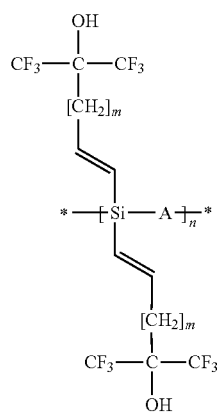

Such fluoroalcohol polycarbosilanes may exhibit selective, reversible absorption of phosphonates or nitrocompounds, as well as pyridyl compounds such as pyridyl substituted aromatics that may reversibly bind with fluorophosphonates or nitrocompounds that may form fluorescent sandwich complexes that may emit at longer wavelengths than the uncomplexed molecules. This may allow for monitoring absorber saturation via fluorescence.

In addition, with reference to FIG. 4, the absorbent layer may be varied over the machine direction (MD) or cross-machine direction (CD) of the substrate. In other words, two or more absorbent layer material compositions may be provided to form the absorber layer, wherein the compositions may be sequentially deposited or deposited in a gradient along either the machine or cross-machine direction of the substrate. It may be appreciated that when the structure is spirally wrapped, the coatings may vary through the radius of the structure or along the axial axis of the structure. See again, FIG. 2. In one example, the absorber materials may be deposited such that the most interactive component, that is, the gas sample constituents exhibiting relatively lower volatility and relatively higher binding energy, may be removed towards the beginning of the flow path, or channels, defined by the structure, and relatively less interactive components, that is, the gas sample constituents exhibiting relatively greater volatility and relatively lower binding energy may be absorbed towards the end of the flow path, or channels, defined by the structure.

The absorbent layer may be provided by various coating and deposition methods such as physical vapor deposition, chemical vapor deposition, various coating processes such as spray coating, doctor blade coating, etc., as well as by electrophoretic deposition. For example, in some embodiments, metal organic frameworks, AgF and carbon particulate materials, may be coated onto the substrate by electrophoretic deposition (EPD). Electrophoretic deposition may be understood as a process wherein colloidal particles suspended in a liquid or other medium may migrate under the influence of an electric field and may deposited either directly or indirectly on an electrode. The fields may be applied in the range of 100V/cm. In addition, the medium may include organic solvents. In other embodiments, the metal organic frameworks and/or carbon may be deposited by electrospray techniques. The coatings may be applied at layer thicknesses of 100 μm or less, including all values and increments in the range of 0.1 μm to 100 μm.

Referring again to FIG. 3, a support layer (illustrated in FIG. 4 as 414) may then be deposited 312 upon the absorber layer (408 of FIG. 4). The support layer may include a metal or ceramic layer and in some examples, the support layer may be a relatively resistive material, capable of heating upon the application of a voltage. Furthermore, the support layer may be deposited by physical vapor deposition, chemical vapor deposition, spray coating, etc. In one example, resistive metal deposition wherein a metal may be raised to its melting point though the use of resistive heating. The metal atoms may then vaporize and travel towards the absorber layer. The metal layer may be relatively continuous, exhibiting porosity, void volume, of less than about 50% by volume, including all values or increments therein. It may be appreciated that the support layer may be relatively resistive and configured to heat upon application of an electric current. The support layer may also be 0.1 μm to 10,000 μm in thickness, including all values and increments therein.

The absorbent layer may be detached 314 from the substrate either before or after the support layer has been applied, by at least partially dissolving the release layer; FIG. 3 illustrates an example where the layer is detached after the support layer has been applied. In addition, the absorbent layer and support layer may be wrapped over a relatively cylindrical or elliptical mandrel 316, which may then be removed 318, forming a hollow cylinder having an external diameter $D_1$ and an internal diameter $D_2$ illustrated in FIG. 2. It may be appreciated that when the structure has been spirally wrapped, the absorbent layer may serve as a layer separator and may fall flush against an opposing support layer surface (416 as illustrated in FIG. 4).

The overall or outer diameter $D_1$ of the spirally wrapped structure may be in the range of 0.1 cm to 10 cm, including all values and increments therein. In addition, inner diameter $D_2$ of the spirally wrapped structure may be in the range of 0.01 cm to 2 cm, including all values and increments therein. Furthermore, the length of a capillary within the column may be in the range of 0.1 meter to 20 meters, including all values and increments therein.

Figure 5:
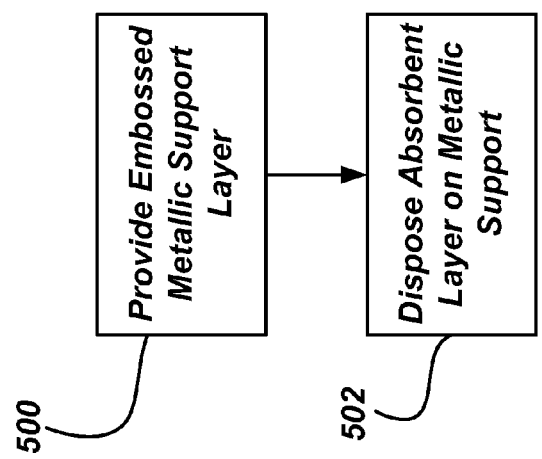
FIG. 5 illustrates an example of a method of forming a spirally wrapped structure illustrated in flow chart form.

In another example, illustrated in FIG. 5, a spirally wrapped structure may be prepared by providing a metallic support layer 500, which may be embossed to include a number of features in the surface. An absorbent layer may then be disposed on the surface 502. In a further example, the substrate may be provided by physical vapor or chemical vapor deposition techniques, spray coating, or other coating techniques onto a patterned surface from which the support layer may be removed.

Figure 6:
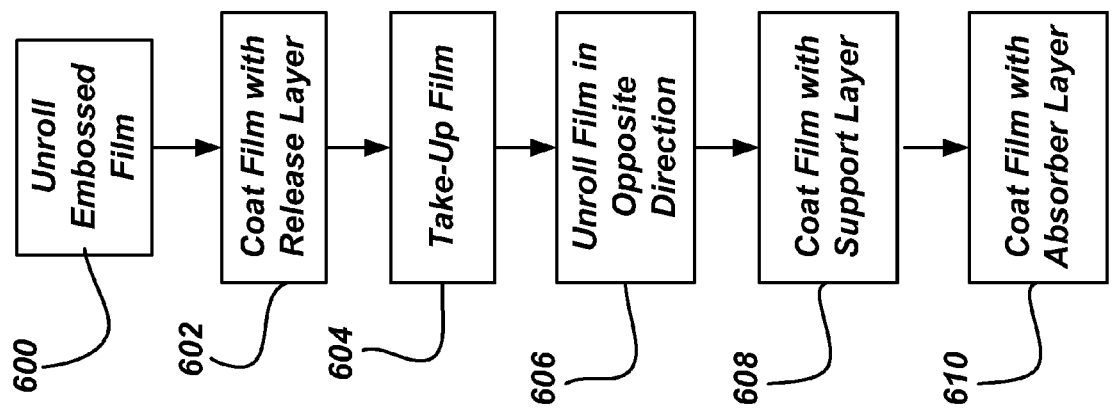
FIG. 6 illustrates an example of a method of forming a spirally wrapped structure illustrated in flow chart form.

In a further example, illustrated in FIG. 6, the column may be produced via a roll to roll vacuum coating technique, wherein a microembossed polymer film may be provided. Reference to microembossed polymer film is reference to a film that includes protruding regions and/or depressed regions which may be used to form the absorber layer as disclosed herein (e.g. channels or other features). An example of such microembossed polymer film may be available from Anvik of Hawthorne, N.Y. The process may include unrolling the film from a first roll 600 and coating the film with a release layer 602 that may include water soluble amorphous or crystalline salt solution on a first surface, from which the solvent may be removed. The film may then be taken up by a second roll 604 and then unrolled from the second roll 606 in the opposite direction such that the second surface may be coated with a support layer 608, such as a metal or other resistive material. The release layer coating and support layer coating may be applied by, for example, a physical or chemical vapor evaporation technique such as vacuum evaporation or e-beam evaporation. The absorber may then be deposited 610 on the support layer by a deposition process as discussed above, including various physical or chemical vapor evaporation techniques or electrophoretic deposition. Then the embossed polymer substrate may be removed. The support layer may be wrapped around a metal coated cylinder which may serve as a contact for application of voltage.

Figure 7:
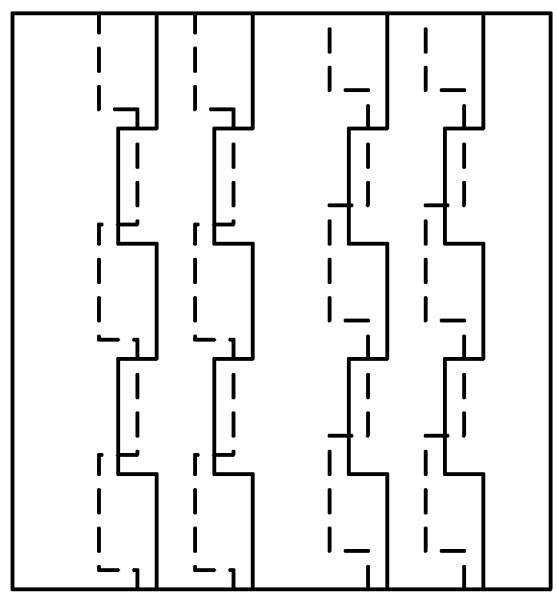
FIG. 7 illustrates an example of a first layer superimposed over a second layer in a spirally wrapped structure, wherein the channels meander.

It may be appreciated that the channels may meander along the length of the channels, i.e., may not be continuously straight in the axial and/or radial direction, preventing the channels from interpenetrating and collapsing into each other as illustrated in FIG. 7. More specifically, FIG. 7 illustrates two superimposed layers of a spirally wrapped structure, the channels defined in the first layer illustrated in broken lines and the channels defined in the second layer illustrated in solid lines meander or are displaced with respect to one another. The amount of displacement may include all or a partial amount of any channel thickness $t_1$ (see again, FIG. 4).

The resulting spirally wrapped structures may be sectioned into chromatography components of 0.1 cm to 10 cm in length, including all values and increments therein and incorporated into the GC system. The spirally wrapped structures may provide flow rates in the range of 50 ml per minute to 30 liters per minute, including all values and increments therein such as 20 liters per minute. In addition the spirally wrapped structures may exhibit a pressure drop of less than 10 atmospheres, including all increments and values in the range of 0.1 to 10 atmospheres, such as 2 atmospheres.

Contacts may be applied either directly or indirectly to the spiral wrapped structures to provide a voltage causing the structures or a resistive component incorporated in the structures to heat. Heating may be controlled by a number of mechanisms including thermal feedback devices, such as thermocouples, and/or controllers. The controllers may be programmable. It may be appreciated that due to the unit size, the gas chromatography system may be operated by a battery system and may be relatively lightweight and small.

Figure 8:
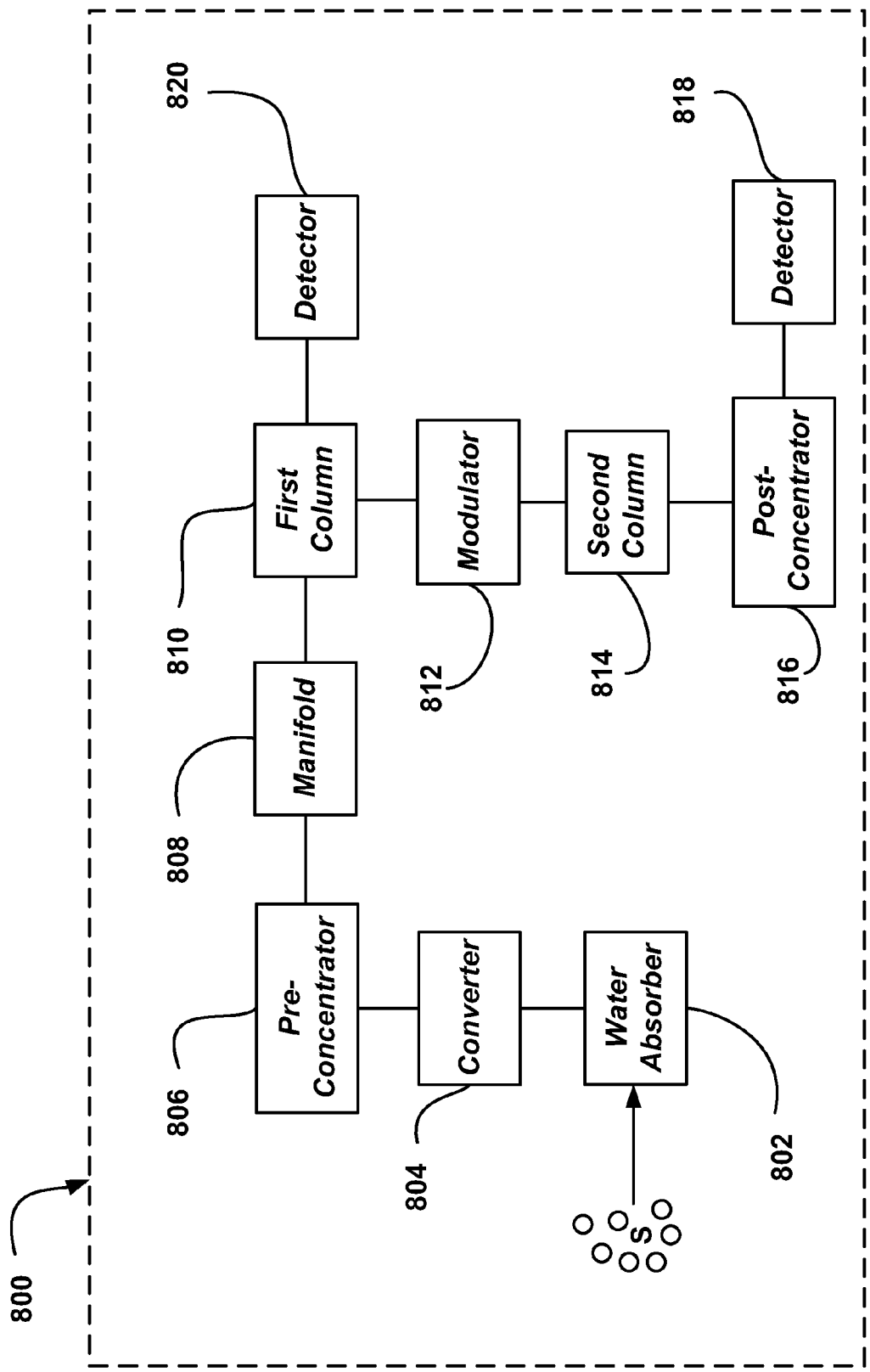
FIG. 8 illustrates an example of a system and method of gas chromatography.

The chromatography system incorporating one or more spirally wrapped structures may operate in a number of configurations. In one example, illustrated in FIG. 8, a gas sample S may be provided in a gas chromatography system 800. The gas sample may be introduced to a water scrubber or trap 802 where excess water may be removed from the sample. As may be appreciated, excess water may compete with analyte absorption, degrade metal oxide frameworks, and induce surface or other reactions between analytes. In one example, a water scrubber may compress a gas sample and then expand the sample driving the sample below the dew point to produce a water aerosol. The sample may be forced into a cycloidal flow with added turbulence to grow the water particles which may be intercepted by a wall with spiral topology. The wall may be formed from a metal interpenetrated with channels exhibiting relatively strong capillary action that may drive the water from the wall to an external surface, which may be spirally wrapped with a metal organic framework configured to selectively reversibly absorb water. When appropriate, such as when the absorbant is saturated, the metal organic framework may then be heated releasing the water and driving it through the porous metal wall into the collecting air stream. An example of a water scrubber is described in U.S. Pat. No. 5,814,128 the teachings of which are incorporated by reference herein. It may be appreciated that the water scrubber or trap may be optional and use may depend on the water levels in the gas sample. If samples are taken from relatively dry environments, w water scrubber or trap may not be necessary.

The gas sample may then be introduced into a converter 804, which may be in fluid communication with the water scrubber. The converter may be provided to chemically convert certain substances or components of the gas sample into other substances. For example, a V to G AgF converter may be used to convert VX (O-ethyl-S-[2-(diisopropylamino)ethyl]-methylphosphonothionate) to its G analog (O-ethyl methyl phosphorofluoridate), which is understood to be relatively more volatile and easily detectable than VX. However, other converters may be utilized, depending on the content of the gas sample. In some embodiments, the converter may be provided as a spirally wrapped structure described above, wherein AgF or other conversion material may be provided as the absorber layer.

The converter may be in fluid communication with a preconcentrator 806, which may collect an analyte from an inlet sample gas stream and eject it on command. In some examples, the preconcentrator may be configured to selectively and reversibly absorb an analyte of interest, such as, for example chemical warfare agents or components in human breath or from metabolic processes. It may be appreciated, that the preconcentrator may be configured to selectively and reversibly absorb other analytes as well. For example, in the case of chemical warfare agents and explosives, the preconcentrator may be configured to absorb fluorophosphonates. The preconcentrator may include a planar (2-D) or 3-D membrane including an absorbent over which an analyte may pass and absorb. The preconcentrator may also include a heater, such as a resistive heater that may heat the membrane providing for desorbtion of the analyte. The heater may be integrated into the membrane or in thermal contact with the membrane. In one example, the preconcentrator may use a metal organic frame work as an absorbent. In another example, the preconcentrator may be a MEMS sized preconcentrator using absorptive carbons placed in a number of dry etched microchannels. An example of a preconcentrator may be available from Supelco. As noted above, in some examples, the preconcentrator may be provided as a spirally wrapped structure as well, wherein the metal oxide framework or absorptive carbons may be provided as the absorber layer.

The sample may enter a first chromatographic column 810 through a manifold 808 system in communication with the preconcentrator. The manifold may be positioned tangentially to the outside of the column and flow inward, or vice versa, i.e., the manifold may be positioned tangentially to the inside of the column and flow outward. The gas sample may pass through the first chromatographic column including a first stationary phase wherein the sample may be at least partially separated into various constituents that may elute from the column at different rates. In some examples, the first stationary phase may be apolar, polar or polarizable as described above. The first chromatographic column may be provided as a spirally wrapped structure wherein the stationary phase may be provided by the absorber layer.

From the first column, the various constituents eluting from the first column may be collected by a thermal or pressure modulator 812 or other splitting device in fluid communication with the first column. In an example of a thermal modulator, sample separation eluting from the first column may be collected and injected into a second chromatographic column 814 in fluid communication with the thermal modulator. The thermal modulator may inject the samples upon application of heat to the modulator. In addition, the modulator may focus a broad band containing several analytes into a narrow band for injection into the second chromatographic column. It may therefore be appreciated that the modulator may provide pressure control or flow rate control for the second column. Furthermore, in some embodiments, the thermal modulator may also be formed from a spirally wrapped structure.

The second chromatographic column 814 may include a second stationary phase, or absorber layer when provided as a spirally wrapped structure. The second stationary phase may be different from the first stationary phase and therefore may include either a different absorber layer or a different absorber layer gradient. In one example, the first chromatography column may include an apolar stationary phase and the second column may include a polar or polarizable stationary phase. In addition, the separation and elution of the constituents may be slightly different from the second column as compared to the first, which may aid in resolving the various constituents which may be present in the gas sample.

It may be appreciated that the gas sample may be carried through the above system in a mobile phase, such as a carrier gas. The carrier gas may be a relatively inert gas or unreactive gas and may include for example, nitrogen, argon, or helium. A post-concentrator 816 may be provided in fluid communication with the second chromatographic column to selectively absorb various eluted constituents from the carrier gas. The post concentrator may also be provided as a spirally wrapped structure. When heated, the post-concentrator may inject or release the absorbed eluted constituents to a detector.

It should be appreciated that the gas sample may be provided to the various components in the gas chromatography system, which may absorb various constituents in the gas sample. In the case of the spirally wrapped structures, the various constituents may be absorbed in the absorber layer, which in the case of a preconcentrator may include a metal organic frame work, or in the case of a stationary phase in a chromatographic column may include a polarizable, polar or apolar coating. In addition, the various components may be heated to release the absorbed material from the columns and/or other elements. It may be appreciated that the absorbed material may desorb or release from the components at different rates upon the application of heat depending on the chemical structure of the constituents and components in the system, the physical properties of the system components and/or other interactions. Heating may be applied relatively uniformly or along a gradient in the columns. In addition, the amount of heat applied or rate of application may change through the elution process.

The eluted constituents of the gas sample may then be provided to one or more detectors 818 and 820, which may be in fluid communication with the first and/or second chromatography columns and may include, for example, mass spectrometers, flame ionization detectors, thermal conductivity detectors, etc. For example, as the various sample constituents elute from the second column, at least a portion of the sample may be diverted to a detector. The detector may assess the amount of constituent detected and/or identify the detected constituents. In one example, multibounce time of flight mass spectrometry may be utilized to determine the composition of the constituents.

The foregoing description of several methods and embodiments has been presented for purposes of illustration. It is not intended to be exhaustive or to limit the claims to the precise steps and/or forms disclosed, and obviously many modifications and variations are possible in light of the above teaching. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. It is intended that the scope of the invention be defined by the claims appended hereto.

What is claimed is:

1. A spirally wrapped chromatographic structure for absorption of analytes, comprising:
   an absorber layer having a first surface and a second surface, wherein one or a plurality of channels are defined in said first surface and wherein said absorber layer comprises two or more material compositions having different binding capabilities to said analytes; and
   a support layer having a first surface and a second surface, wherein said absorber layer and support layer are spirally wrapped wherein the first surface of the support layer is disposed on said second surface of said absorber layer, wherein said absorber layer and said support layer comprise a spiral configuration such that at least a portion of said first surface of said absorber layer contacts at least a portion of said second surface of said support layer and said channel(s) are arranged radially around the structure;
wherein said support layer comprises an electrically resistive material at a thickness of 0.1 μm to 10,000 μm and capable of heating upon the application of a voltage and wherein said spirally wrapped chromatographic structure is configured to provide a flow rate in the range of 50 ml per minute to 30 liters per minute.

2. The structure of claim 1, wherein said structure is a chromatography column and said absorber layer is a stationary phase of said chromatography column.

3. The structure of claim 1, wherein said channels are 0.1 μm to 10,000 μm in thickness and/or in depth.

4. The structure of claim 1, wherein said at least two material compositions, vary with respect to McReynold's values along the axial axis or radius of said structure.

5. The structure of claim 1, wherein said absorber layer comprises a fluoroalcohol polycarbosilane and/or fluoroalcohol polycarbosiloxane.

6. The structure of claim 1 wherein said absorber layer comprises:

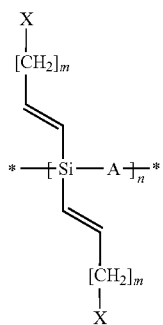

where n has a value of 10-10,000 m has a value of 1-50, and X is a carbon atom or an aromatic ring which carbon atom or aromatic ring includes at least one of an alcohol group (—OH) and a —CF$_3$ group, and A is selected from the following: —O—, —(CH$_2$)$_x$— where x has a value of 1-3, and/or A is an aromatic group.

7. The structure of claim 1 wherein the absorber layer comprises:

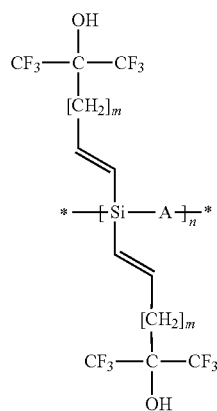

where n has a value of 10-10,000 m has a value of 1-50, and A is selected from the following: —O—, —(CH$_2$)$_x$— where x has a value of 1-3, and/or A is an aromatic group.

8. The structure of claim 1, wherein said absorber layer comprises AgF.

9. The structure of claim 1, wherein said absorber layer comprises metal organic frameworks.

10. A system for chromatographic analysis of analytes, comprising:
a first chromatography column, wherein said first chromatography column comprises a first spirally wrapped structure including a first absorber layer having a first absorber layer first surface and a first absorber layer second surface, wherein one or a plurality of channels are defined in said first absorber layer first surface and wherein said first absorber layer comprises two or more material compositions having different binding capabilities to said analytes, and a first support layer having a first support layer first surface and a first support layer second surface, the first support layer first surface being disposed on said first absorber layer second surface, wherein said first absorber layer and said first support layer are rolled into a spiral configuration such that at least a portion of said first absorber layer first surface contacts at least a portion of said first support layer second surface and said channel(s) are arranged radially around the structure, said first support layer comprising an electrically resistive material at a thickness of 0.1 μm to 10,000 μm capable of heating upon application of a voltage; and
a detector in fluid communication with said first chromatography column and wherein said column is configured to provide a flow rate in the range of 50 ml per minute to 30 liters per minute.

11. The system of claim 10, further comprising a second chromatography column including a second absorber layer, wherein:
said first absorber layer is different that said second absorber layer; and
said second chromatography column is in fluid communication with said first chromatography column.

12. The system of claim 10 further comprising a preconcentrator in fluid communication with said first chromatography column, said preconcentrator comprising a second spirally wrapped structure including a second absorber layer having a second absorber layer first surface and a second absorber layer second surface, wherein one or a plurality of channels are defined in said second absorber layer first surface and a second support layer having a second support layer first surface and a second support layer second surface, the second support layer first surface being disposed on said second absorber layer second surface, wherein said absorber layer and said support layer are rolled into a spiral configuration such that at least a portion of said second absorber layer first surface contacts at least a portion of said second support layer second surface.

13. The system of claim 10 further comprising a water scrubber in communication with said first chromatography column, said water scrubber comprising a second spirally wrapped structure including a second absorber layer having a second absorber layer first surface and a second absorber layer second surface, wherein one or a plurality of channels are defined in said second absorber layer first surface and a second support layer having a second support layer first surface and a second support layer second surface, the second support layer first surface being disposed on said second absorber layer second surface, wherein said absorber layer and said support layer are rolled into a spiral configuration such that at least a portion of said second absorber layer first surface contacts at least a portion of said second support layer second surface.

14. The system of claim 10, further comprising a thermal or pressure modulator in communication with said first chromatography column, said thermal or pressure modulator comprising a second spirally wrapped structure including a second absorber layer having a second absorber layer first surface and a second absorber layer second surface, wherein one or a plurality of channels are defined in said second absorber layer first surface and a second support layer having a second support layer first surface and a second support layer second surface, the second support layer first surface being disposed on said second absorber layer second surface, wherein said absorber layer and said support layer are rolled into a spiral configuration such that at least a portion of said second absorber layer first surface contacts at least a portion of said second support layer second surface.

15. The system of claim 10, further comprising a post-concentrator in communication with said first chromatography column, said post-concentrator comprising a second spirally wrapped structure including a second absorber layer having a second absorber layer first surface and a second absorber layer second surface, wherein one or a plurality of channels are defined in said second absorber layer first surface and a second support layer having a second support layer first surface and a second support layer second surface, the second support layer first surface being disposed on said second absorber layer second surface, wherein said absorber layer and said support layer are rolled into a spiral configuration such that at least a portion of said second absorber layer first surface contacts at least a portion of said second support layer second surface.

16. The system of claim 10, wherein said detector is a mass spectrometer.

17. The system of claim 16, wherein said detector is a multi-bounce time of flight mass spectrometer.

* * * * *